US006485518B1

United States Patent
Cornwall et al.

(10) Patent No.: US 6,485,518 B1
(45) Date of Patent: Nov. 26, 2002

(54) FACET SCREW AND BONE ALLOGRAFT INTERVERTEBRAL SUPPORT AND FUSION SYSTEM

(75) Inventors: Bryan Cornwall, San Diego, CA (US); James F. Marino, La Jolla, CA (US); Dan Ahlgren, San Diego, CA (US); Troy Wooley, San Diego, CA (US)

(73) Assignee: NuVasive, San Diego, CA (US)

( * ) Notice: Subject to any disclaimer, the term of this patent is extended or adjusted under 35 U.S.C. 154(b) by 0 days.

(21) Appl. No.: 09/735,276

(22) Filed: Dec. 11, 2000

Related U.S. Application Data

(60) Provisional application No. 60/172,849, filed on Dec. 10, 1999.

(51) Int. Cl.⁷ .......................... A61F 2/44; A61B 17/70
(52) U.S. Cl. ...................... 623/17.11; 128/898; 606/61
(58) Field of Search .................... 623/17.11, 17.12, 623/17.13, 17.14, 17.15, 17.16; 128/898; 606/86, 96, 99, 104, 61

(56) References Cited

U.S. PATENT DOCUMENTS 5,527,312 A  6/1996 Ray
6,045,580 A  4/2000 Scarborough et al.

FOREIGN PATENT DOCUMENTS

EP       667127      8/1995
WO    WO 99/38461    8/1999

OTHER PUBLICATIONS

Benini et al., "Undercutting decompression and posterior fusion with translaminar facet screw fixation in degenerative lumbar spinal stenosis: Technique and results" (1995) *Neuro–Orthopedics* 17/18:159–172.
Kambin et al., "History and current status of percutaneous arthroscopic disc surgery" (1996) *Spine* 21(24S):57S–61S.
Stein et al., "Percutaneous facet joint fusion: Preliminary experience" (1993) *Journal of Vascular and Interventional Radiology* 4(10):69–74.
Vamvanij et al., "Surgical treatment of internal disc disruption: An outcome study of four fusion techniques" (1998) *Journal of Spinal Disorders* 11(5):375–382.

*Primary Examiner*—David J. Isabella
(74) *Attorney, Agent, or Firm*—Jonathan Spangler

(57) ABSTRACT

An intervertebral support assembly, comprising a pair of bone allografts positioned between two adjacent vertebrae, the bone allografts being positioned towards the anterior portion of the adjacent vertebrae; and a pair of facet screws, each facet screw securing together a facet joint between the two adjacent vertebrae.

A method of providing support between two adjacent vertebrae, comprising positioning a pair of bone allografts between the two adjacent vertebrae at a location towards the front of the adjacent vertebrae; and securing together facet joints between the two adjacent vertebrae with a pair of facet screws.

24 Claims, 8 Drawing Sheets

FACET SCREW AND BONE ALLOGRAFT INTERVERTEBRAL SUPPORT AND FUSION SYSTEM

CROSS-REFERENCES TO RELATED APPLICATIONS

This application is a continuation of, and claims the benefit of priority from U.S. application No. 60/172,849, filed on Dec. 10, 1999, the full disclosure of which is incorporated herein by reference.

TECHNICAL FIELD

The present invention relates to intervertebral support systems, and to systems for promoting intervertebral bone fusion.

BACKGROUND OF THE INVENTION

A variety of support assemblies currently exist which may be surgically implanted into a patient's intervertebral space so as to provide support between two (or more) adjacent vertebrae. Surgical implantation of such systems is typically used to provide support along the spinal column in cases where a portion of the patient's intervertebral anatomy has become diseased or destroyed. In addition, such support systems are also commonly used following a diskectomy, wherein the patient's intervertebral disk is surgically removed.

A drawback of these existing support systems is that they tend to be somewhat large and bulky, especially when these systems operate to provide support across a large portion of the patient's vertebral region. Being large and bulky, surgical implantation of these systems into a patient's vertebral region often creates a substantial amount of trauma to the patient.

Moreover, the installment of such large, bulky support systems into a patient's intervertebral space typically also requires a large amount of tissue to first be removed from the patient's intervertebral space so as to make way for the device.

Most commonly, existing support systems typically operate by inhibiting (normal) movement between the adjacent vertebrae, thereby holding these vertebrae at fixed positions relative to one another, with the mechanical body of the supporting structure providing the needed support along the patient's spinal column. Such supporting systems are typically made of stainless steel or titanium, and are designed to permanently remain within the patient's body.

SUMMARY OF THE INVENTION

The present invention provides a novel system of intervertebral support using a pair of bone allografts and a pair of facet screws.

An advantage of the present system is that, by inhibiting motion between two adjacent vertebrae, it facilitates natural bone fusion between these vertebrae. An advantage of the present invention's use of bone allografts (positioned between the vertebrae) is that these allografts will eventually be resorbed into the patient's body as bone growth between the immobilized vertebrae progresses. In contrast, existing mechanical (e.g.: metallic) intervertebral support structures simply remain as large permanent foreign structures within the patient's body. In preferred aspects, motion between the two adjacent vertebrae is specifically inhibited by the facet screws, as will be explained.

The present system advantageously provides intervertebral support at three locations in particular, with these three locations together forming a triangle. Specifically, each of the facet screws provides support at the facet joints (which are disposed at two symmetrically spaced apart locations at the posterior or rear of the vertebral column). The bone allografts are preferably positioned to provide support at an anterior (i.e. front), central location in the vertebral column. An advantage of the present three point (i.e.: triangular) support system is that support is provided in three perpendicular directions, (thereby providing support with respect to forward-backward bending, side-to-side bending and torsion of the spine). Furthermore, the present three point (i.e.: triangular) support system provides support at three separate locations which are spaced apart over a relatively large section of the patient's spinal column, providing enhanced stability. Specifically, the three sides of the present support triangle correspond to the locations of the two facet joints and the inter vertebral disc.

An important advantage of the present system is that it can be assembled in a minimally invasive percutaneous (preferably cannulated) surgical approach. In contrast, existing systems which provide support across a wide area of the patient's vertebrae typically comprise a single large integrated structure which substantially fills the patient's intervertebral space, and which is typically installed during a major invasive open surgical procedure. A further advantage of the present assembly is that since it comprises four separate components, (two bone allografts and two facet screws), these four components can be installed sequentially, with each of the components being installed through a cannula. In contrast, existing intervertebral support systems typically comprise a single large assembly which cannot be installed through a cannula.

In preferred aspects, the two bone allografts are positioned at an angle to one another. An advantage of having the bone allografts disposed angled to one another is that they provide support in perpendicular directions (i.e.: along two axes which are angled to one another). Specifically, in a preferred case using long, narrow shaped bone allografts, the bone allografts are preferably positioned with their long central longitudinal axes disposed at an angle to one another.

Since the present pair of bone allografts are positioned at an angle to one another, tall, narrow bone allografts can be used. Advantages of using a tall, narrow bone allograft include its fabrication requiring less bone material than would be used in conventionally manufactured allografts (which tend to be both flatter and wider, or large in diameter and length, e.g.: cylindrical). In addition, the present narrow bone allografts are more easily inserted into the patient through a (narrower) cannulated passageway.

In preferred aspects, two cannulae are used for positioning the pair of bone allografts, with the cannulae positioned at opposite posterolateral angles to one another. One cannula is used to position the first bone allograft and one cannula is used to position the second bone allograft. In this aspect, the angle between the bone allografts preferably corresponds to the angle between the cannulae. Accordingly, each of the bone allografts can be inserted directly into the patient's intervertebral space in a relatively straight path through the cannula(e) and into the patient's intervertebral space. As such, the present pair of bone allografts are easily positioned at a preferred angle to one another when initially deployed in a percutaneous posterolateral approach procedure. Moreover, in preferred aspects, the bone allografts can be inserted into the intervertebral space and then rotated by approximately 90° to achieve vertebral distraction, tensioning the annulus and opening the foramen, thereby decompressing the nerve root.

As stated above, in a preferred aspect of the present invention, both the bone allografts and the facet screws are positioned in the patient's spinal region through a posterolateral minimally invasive approach, which may optionally include a cannulated approach.

Prior to installing the present bone allografts and facet screws, a portion (or all) of the patient's intervertebral disk may be removed (i.e.: a "diskectomy" may be performed). Thereafter, the opposite vertebral endplates of the adjacent vertebrae may optionally be decorticated, which may produce a natural healing (bone fusion) response, if desired.

Thereafter, and in accordance with the present invention, the pair of bone allografts are positioned in the patient's intervertebral space. Preferably the bone allografts are inserted through posterolaterally introduced cannulae. In preferred aspects, two cannulae are used, with one positioning each bone allograft; however, the use of a single cannula to place the two bone allografts one after another (in opposite posterolateral approaches) is also contemplated. Additionally, the two bone allografts could be placed through one cannula positioned from only one posterolateral direction. Advantageously, each of the pair of bone allografts can be positioned (i.e.: inserted into the intervertebral space) through a separate cannula with the posterolateral angle at which the cannulae are disposed corresponding to the angle between the bone allografts.

Preferably, after the bone allografts have been positioned between the adjacent vertebrae, the bone allografts will support the vertebrae, causing the vertebrae to move into a natural lordotic angle limiting facet joint movement such that it becomes easier to insert the facet screws.

The present facet screws are used to secure a patient's facet joints together, thus preventing relative movement therebetween. An advantage of using facet screws is that they provide stabilization to the spine, but are not as surgically time consuming to install as, for example, pedicle screws. Another advantage of the present system is that, by immobilizing adjacent facet joints, it provides stability for vertebral arthrodesis between the adjacent vertebrae.

In accordance with the present invention, therefore, a system is provided to position a facet screw to secure a patient's opposite adjacent first and second facet joints together, and to promote fusion therebetween. Each of the facet screws may preferably be positioned such that it passes through, and locks together, the superior articular process of one vertebrae with the inferior articular process of an adjacent vertebrae. Preferably, the threads of the facet screw extend all the way into the pedicle, thus providing increased anchoring strength. This embodiment is called the transfacet approach. Other approaches for facet screw placement are also contemplated (i.e. the translaminar approach) within the scope of the present invention.

Accordingly, each of the facet screws provides support at an opposite posterior (rear) side of the patient's vertebral column. Together with the bone allografts, which provide support at the anterior (front center) of the vertebral column, the present system of two bone allografts and two facet screws, provides a "triangular" support structure.

In an optional preferred aspect of the invention, autologous bone graft material is harvested from the patient and is delivered percutaneously into the patient at a location adjacent to the bone allografts. Specifically, the autologous bone graft material may be positioned both behind the allografts (i.e.: within the V-shape formed by the two allografts) and to the rear of the bone allografts (i.e.: behind the allografts in their posterolateral direction of approach). In preferred aspects, the autologous bone graft material may be harvested from the patient's iliac crest. Such harvesting of bone graft material directly from the patient's iliac crest is especially advantageous when the minimally invasive approach used passes through the patient's iliac crest, with bone material being removed from the iliac crest to provide cannulated access to the patient's intervertebral space.

In preferred aspects, the present bone allografts are dimensioned with a height of 0.20 to 0.75 inches, a width of 0.20 to 0.75 inches, and a length of 0.60 to 1.20 inches. In one particular preferred aspect, the present bone allografts are dimensioned with a height of about 0.40 inches, a width of about 0.25 inches, and a length of about 0.80 inches.

In preferred aspects, the height to width ratio of the allografts is about 1.2 to 2.0. In more preferred aspects, the height to width ratio of the allografts is about 1.4 to 1.8. In more preferred aspects, the height to width ratio of the allografts is about 1.6.

In preferred aspects, the bone allografts are positioned between adjacent vertebrae by an inserter. Optionally, a two pronged inserter may be used with each of the bone allografts held between the prongs of the inserter. In preferred aspects, the bone allografts may be formed with lateral gooves in which the prongs of the inserter are received.

In optional preferred aspects, the bone allografts may be formed with a curved front edge such that they can be positioned near the outer (front) perimeter of the intervertebral space, thereby advantageously resting on the hard cortical bone at the perimeter of the vertebrae. Most preferably, each of the bone allografts are formed such that their curved front end is the hardest portion of the bone allograft, thereby providing greatest support around the curved front end of the allograft.

In optional aspects, the positioning of the bone allografts may also involve distraction of the vertebrae, which may be performed by the inserter itself, by the shape of the bone allograft itself, or by additional tools (which may also be received through the cannula(e).

In accordance with the present invention, the two facet screws are also positioned in a percutaneous posterolateral approach (which may optionally be cannulated).

In preferred aspects, the cannulae (through which both the bone allografts and the facet screws are advanced) are positioned with the assistance of a surgical guideframe.

DESCRIPTION OF THE SPECIFIC EMBODIMENTS

The present invention comprises an intervertebral support system and a method of installing an intervertebral support system.

In preferred aspects, the present invention comprises an intervertebral support assembly, comprising, a pair of bone allografts positioned between two adjacent vertebrae, with the bone allografts being positioned towards the front of the adjacent vertebrae; and a pair of facet screws, each facet screw securing together a facet joint between the two adjacent vertebrae.

Figure 1:
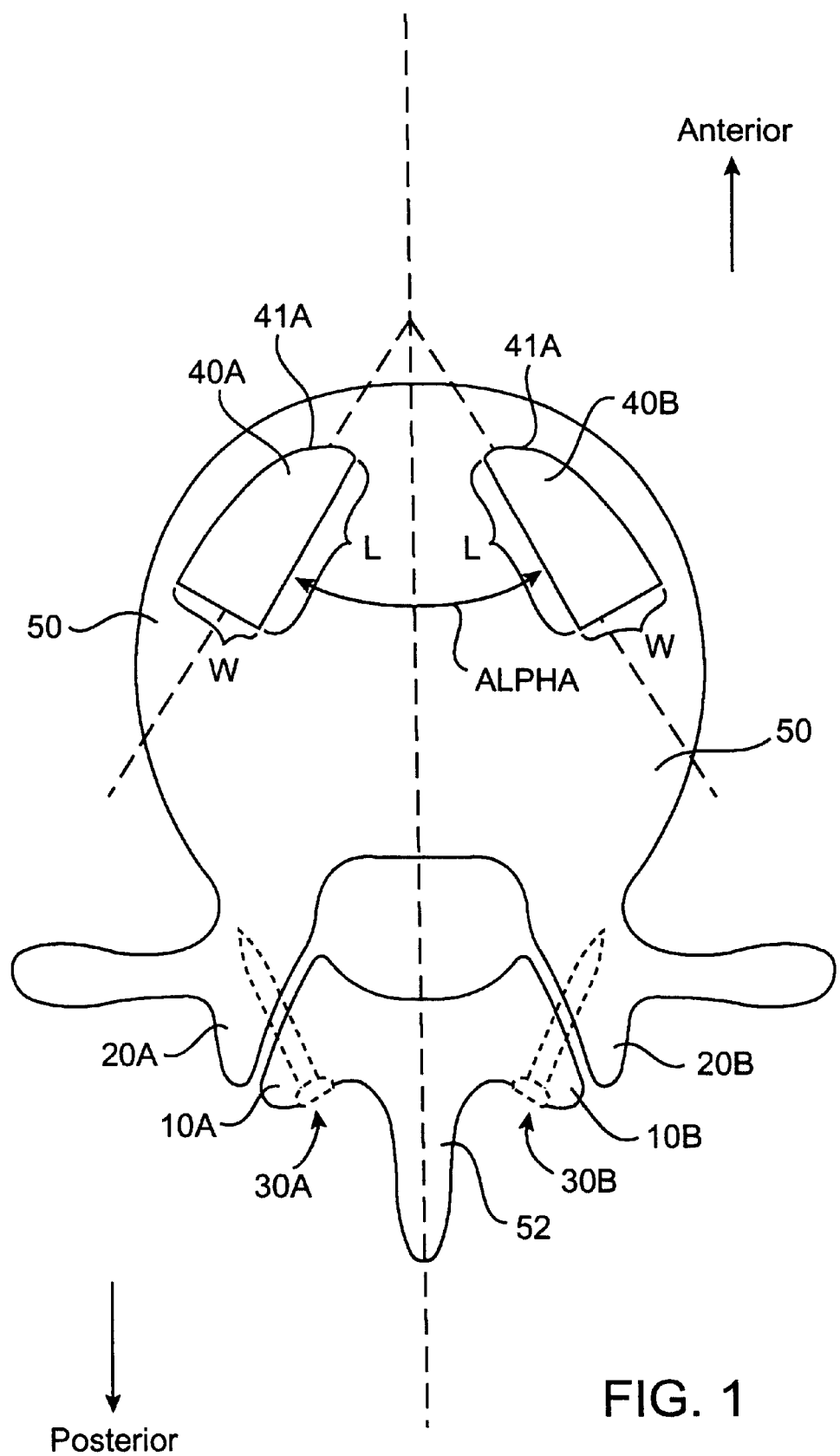
FIG. 1 is a top view of the present support system showing first and second facet joints held together by facet screws, and showing placement of first and second bone allografts.
Figure 2:
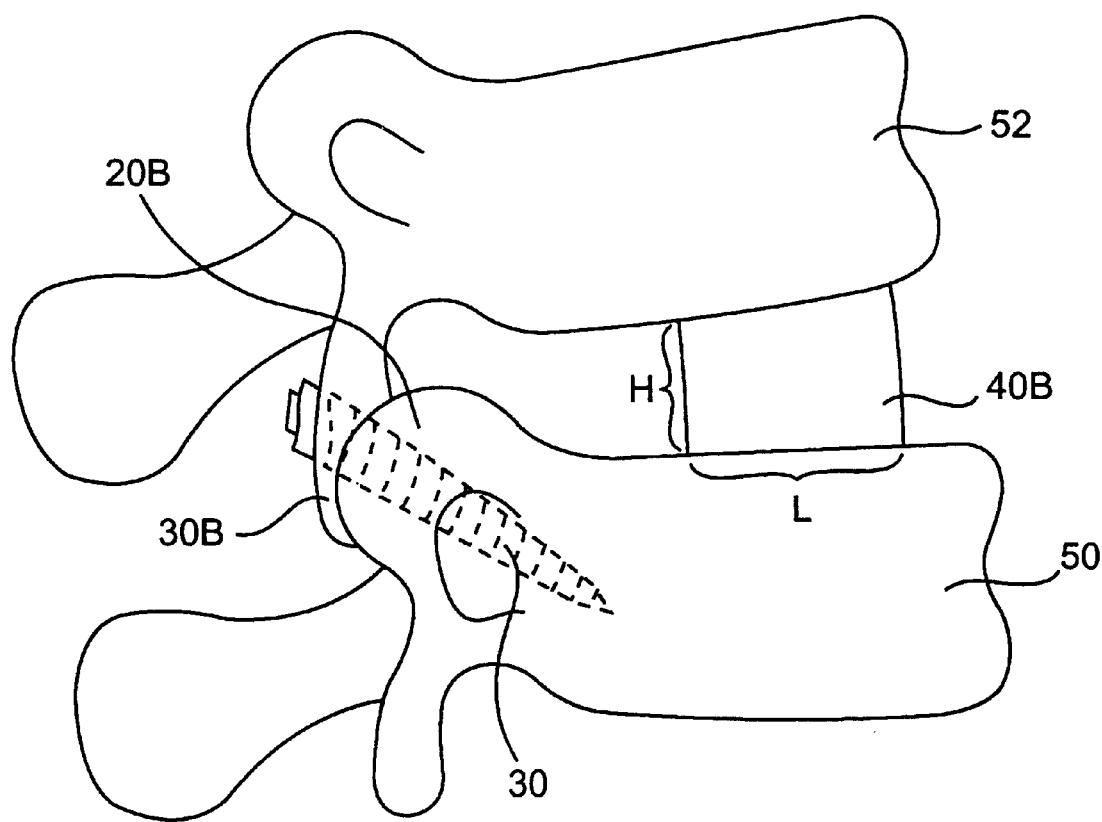
FIG. 2 is a side view of the present support system, as positioned between two adjacent vertebrae.

Referring to FIGS. 1 and 2, the present invention is shown as follows. A pair of bone allografts 40A and 40B are provided. Bone allografts 40A and 40B are preferably positioned between adjacent vertebrae 50 and 52. Most preferably, bone allografts 40A and 40B are positioned at an anterior location (i.e.: towards the front of adjacent vertebrae 50 and 52). In addition, bone allografts 40A and 40B are preferably positioned near the curved outer perimeter (front, and or sides) of the intervertebral space, as shown.

As can be seen in FIG. 1, bone allografts 40A and 40B may preferably be positioned at an angle ALPHA to one another. In preferred aspects, angle ALPHA is approximately 30° to 160°. Most preferably, angle ALPHA is approximately 90° to 120°.

As can be seen in FIGS. 1 and 2, each bone allograft 40A/40B has a length L, a width W and a height H, as shown. By positioning bone allografts 40A and 40B at angle ALPHA to one another, support is provided both in an anterior-posterior (i.e.: front-to-back) and in a lateral (i.e.: side-to-side) direction. The angling of bone allografts 40A and 40B to one another is especially advantageous when providing support when bone allografts 40A/40B are dimensioned to be narrow (i.e.: have a small W value), and also when they are tall and narrow (i.e.: have a large H value as well).

In preferred aspects, bone allografts 40A and 40B have a preferred length L from 0.60 to 1.20 inches, a preferred width W from 0.20 to 0.75 inches, and a preferred height H from 0.20 to 0.75 inches.

Figure 8:
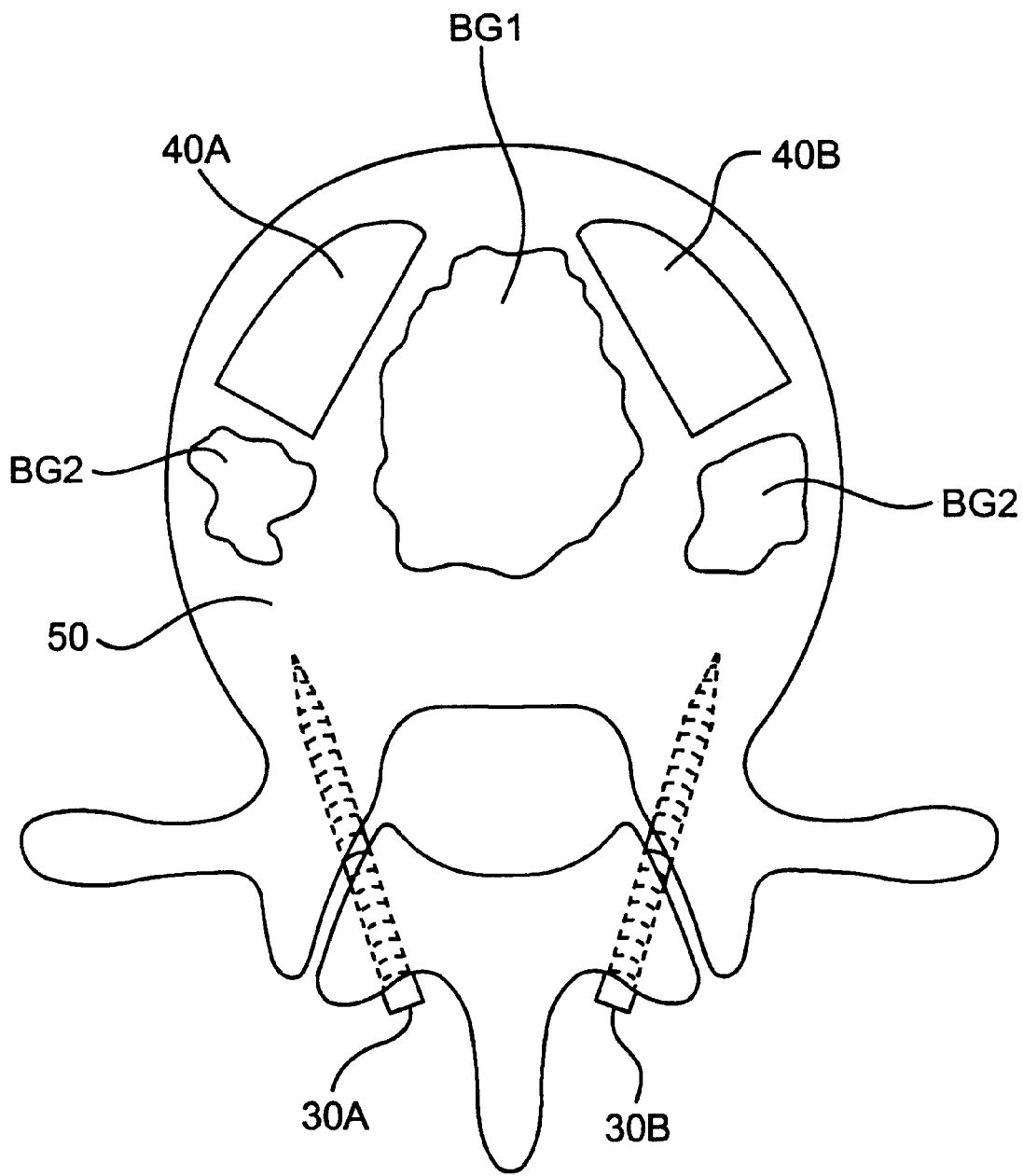
FIG. 8 corresponds to FIG. 1, but shows the additional placement of autologous bone graft material in the patient's intervertebral space.

In an optional aspect, shown in FIG. 8, autologous bone graft material BG is positioned between and to the rear of bone allografts 40A and 40B (i.e.: BG1) and is also positioned behind (in a posterolateral approach) each of bone allografts 40A and 40B (i.e.: BG2). The positioning of autologous bone graft material BG offers the advantage of promoting intervertebral bone fusion.

In optional preferred aspects, bone allografts 40A and 40B may comprise bone block systems as set forth in copending U.S. Regular patent application, Ser. No. 09/320,081, filed May 26, 1999, and Provisional Patent application, No. 60/120,663, filed Feb. 19, 1999, and incorporated herein by reference in their entirety for all purposes. For example, placement of bone allografts 40A and 40B may be accomplished using any of the inserters, or insertion techniques as set forth in these applications.

Moreover, bone allografts 40A and 40B may be stored in saline prior to use in accordance with the systems set forth in copending U.S. Regular patent application, Ser. No. 09/687,611, filed Oct. 11, 2000, and Provisional Patent application, No. 60/226,660, filed Aug. 21, 2000, and incorporated herein by reference in their entirety for all purposes.

As can also be seen, facet screws 30A and 30B are used to secure together first facet joints (10A and 10B) and second facet joints (20A and 20B). As illustrated, facet screws 30 are positioned in a transfacet manner disposed in a posterior approach with respect to the patient, however, other approaches such as a translaminar approach are also contemplated within the scope of the present invention. In the present transfacet approach of FIG. 1, first facet joint 10 preferably comprises a patient's inferior articular process and second facet joint 20 comprises a patient's superior articular process. When tightened into position, facet screws 30A and 30B will immobilize first facet joint 10 and second facet joint 20 together.

Facet screws 30A and 30B can be any form of commercially available facet screws but may also include facet screws positioned in accordance with the novel system set forth in copending U.S. Regular patent application Ser. No. 09/549,807, filed Apr. 14, 2000, and incorporated herein by reference, in which a system for ablating the opposing faces of the facet joints (so as to induce bone growth therebetween) is also set forth.

The present system also sets forth a preferred method of installing the present assembly. In a preferred aspect, the present invention comprises a method of providing support between two adjacent vertebrae 50 and 52, comprising positioning a pair of bone allografts 40A and 40B between the two adjacent vertebrae 50 and 52 at a location towards the front of the adjacent vertebrae; and securing together facet joints 10A and 10B between the two adjacent vertebrae 50 and 52 with a pair of facet screws 30A and 30B.

In preferred aspects, placement of each of bone allografts 40A and 40B and facet screws 30A and 30B is accomplished in a cannulated approach, as follows.

Figure 3:
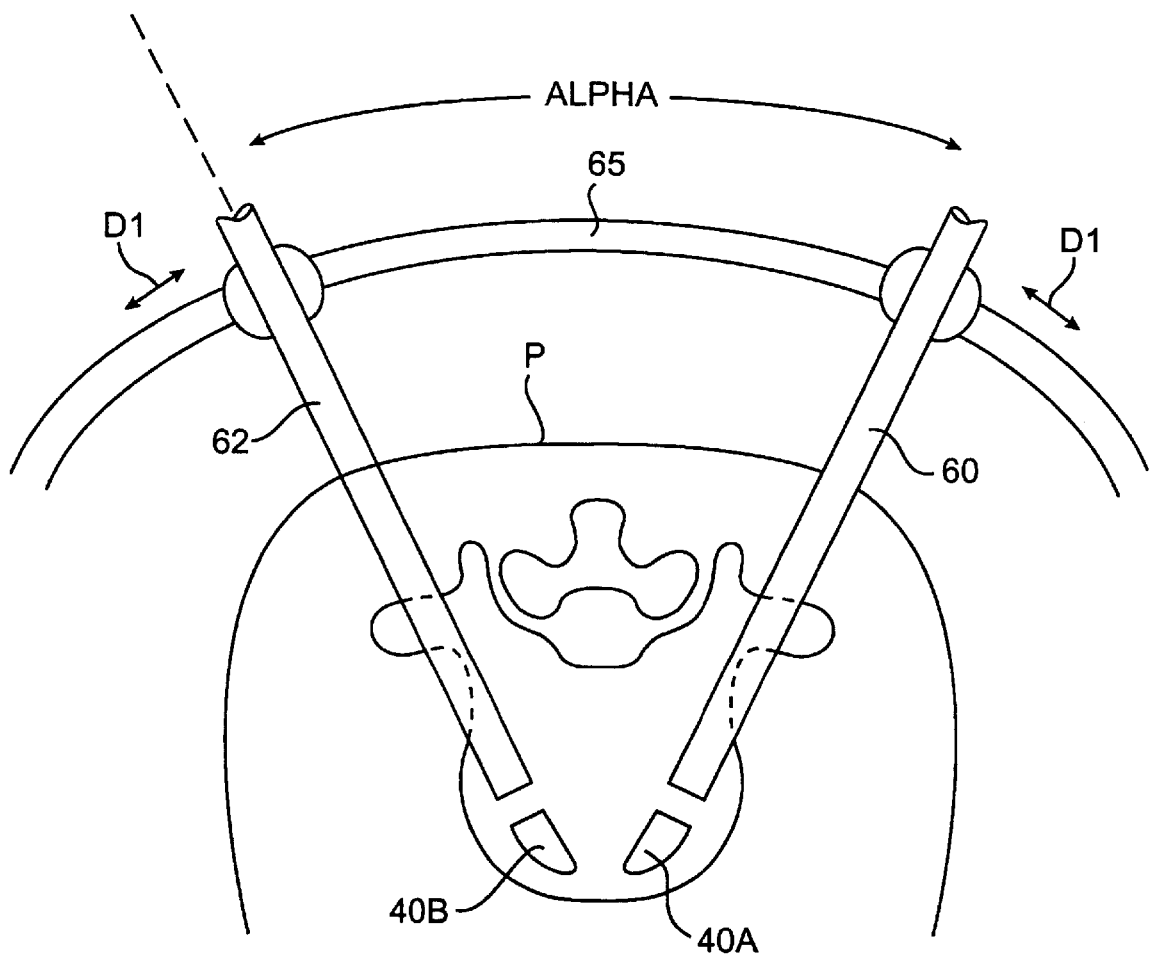
FIG. 3 is an illustration of placement of a pair of bone allografts with the assistance of a polar coordinate surgical guideframe.

Referring to FIG. 3, placement of bone allografts 40A and 40B with a polar coordinate surgical guideframe is seen. An example of such a polar coordinate surgical guideframe 60 is set forth in copending U.S. Provisional Patent application No. 60/213,730, filed Jun. 22, 2000, and incorporated herein by reference in its entirety. In this aspect of the invention, cannulae 62 and 64 are positioned at posterolateral angles to patient P, as shown. Preferably, each of cannulae 62 and 64 is moved along curved member 65 in curved direction D1 to a position such that cannulae 62 and 64 are positioned at (or near) angle ALPHA to one another. Therefore, when bone allografts 40A and 40B are advanced in a straight path through respective cannulae 62 and 64, bone allografts 40A and 40B will be positioned at preferred angle ALPHA to one another.

In optional preferred aspects, the positioning of autologous bone graft material BG between and to the rear of bone allografts 40A and 40B (i.e.: BG1) and/or positioned behind (in a posterolateral approach) each of bone allografts 40A and 40B (i.e.: BG2) is carried out be passing bone graft material BG through cannulae 60 and 62 after bone allografts 40A and 40B have been positioned.

Figure 5:
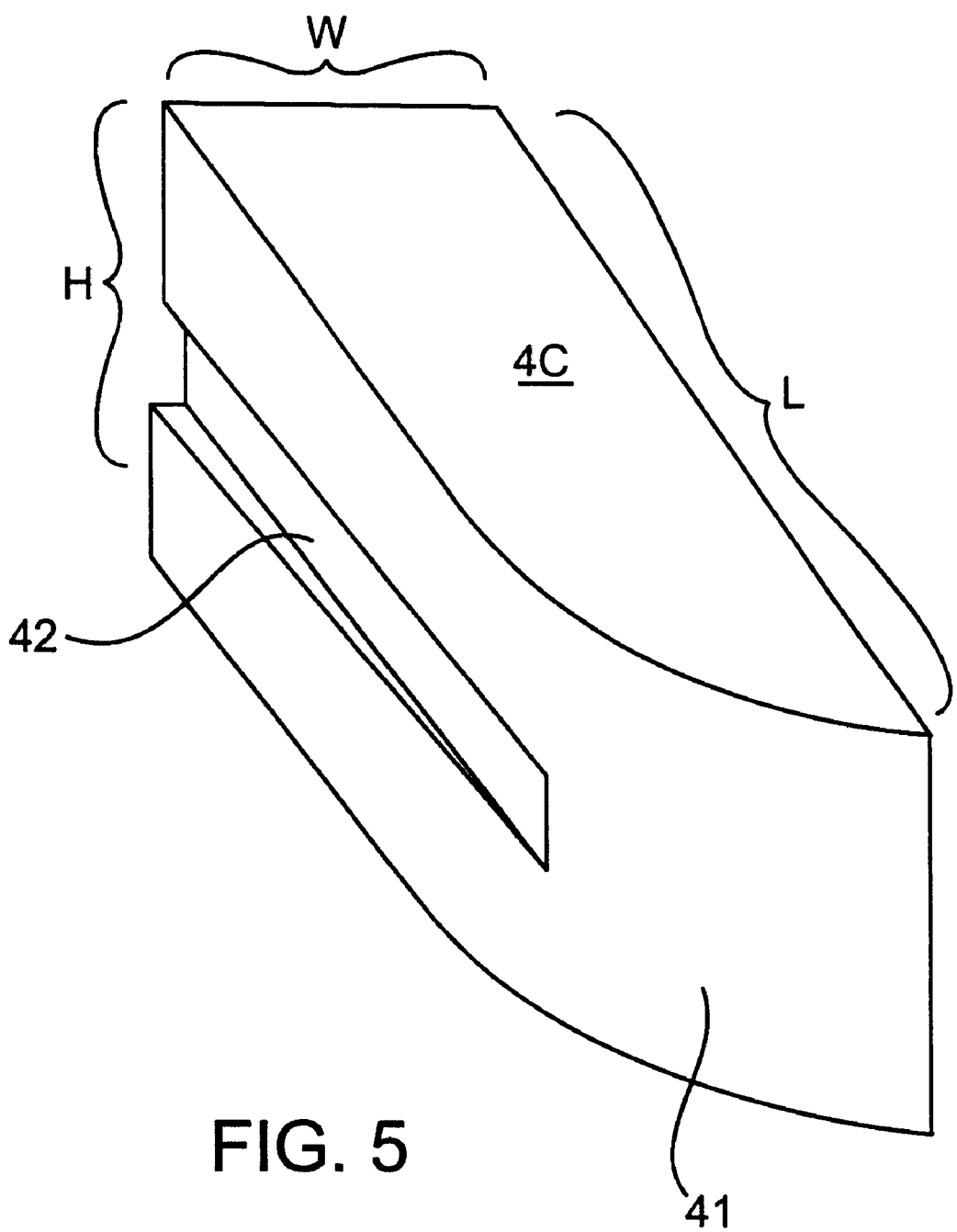
FIG. 5 is a front perspective view of one of the bone allografts.
Figure 6:
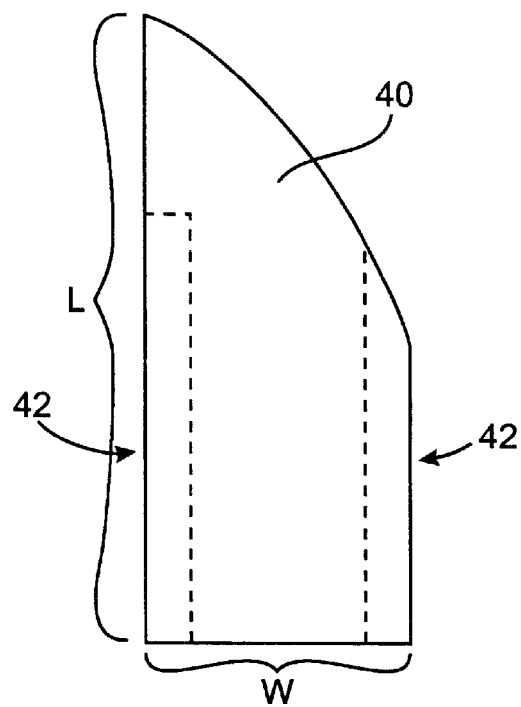
FIG. 6 is a top plan view of a bone allograft and an inserter.
Figure 6:
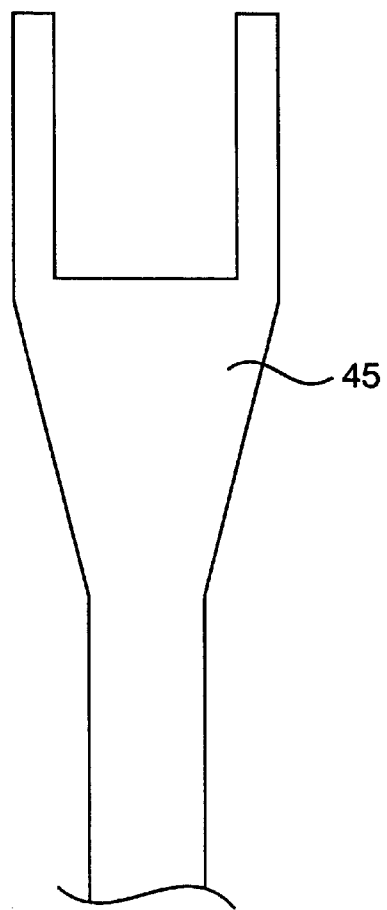
Figure 7:
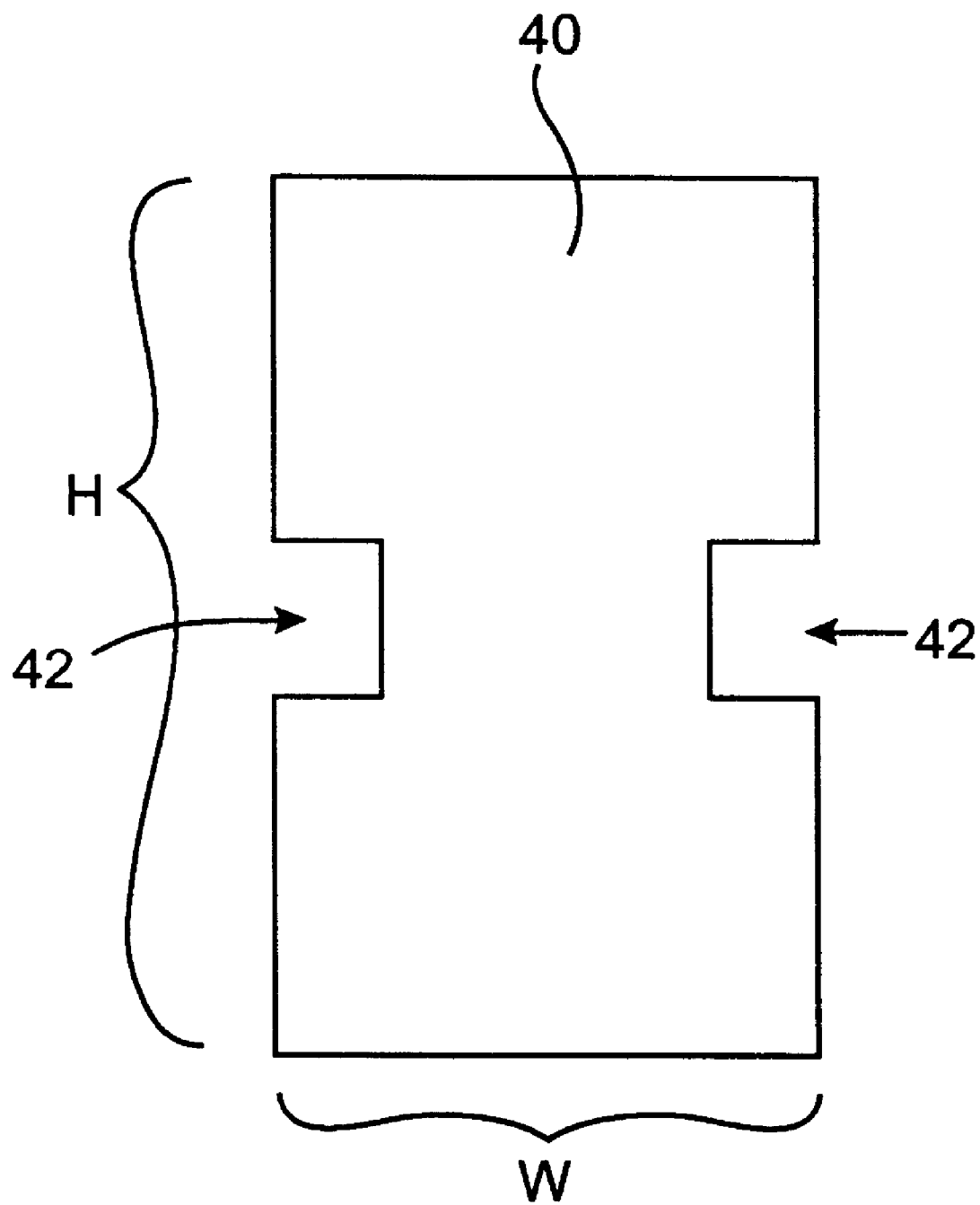
FIG. 7 is a rear view of a bone allograft.

As shown in FIGS. 5, bone allograft 40 preferably has a curved front end 41 such that, when positioned between vertebrae 50 and 52, it can be positioned close, very close or adjacent to, the curved outer perimeter of the vertebrae, as shown in FIG. 1. Bone allograft 40 may optionally have lateral (i.e.: side) grooves 42 extending therealong. As shown in FIG. 6 and 7, grooves 42 may be used for holding bone allograft 40 between the prongs of a two prong inserter 45 which may be used to advance bone allograft 40 into position. In optional preferred aspects, advance bone allograft 40 is advanced into the patient's intervertebral space on its side (with dimension H being parallel to vertebrae 50 and 52). Thereafter, inserter 45 may be rotated by about 90° such that bone blocks 40 are positioned as shown in FIG. 1. An advantage of this is that bone allografts 40A and 40B may each be inserted prior to full distraction (with tall, narrow bone allografts 40A and 40B initially inserted on their sides, thereby fitting easier into the patient's intervertebral space prior to distraction of the vertebrae. In optional preferred aspects, the actual rotation of allografts 40A and 40B assists in distraction of the vertebrae 50 and 52 as the tall, narrow allografts are stood upright.

Figure 4:
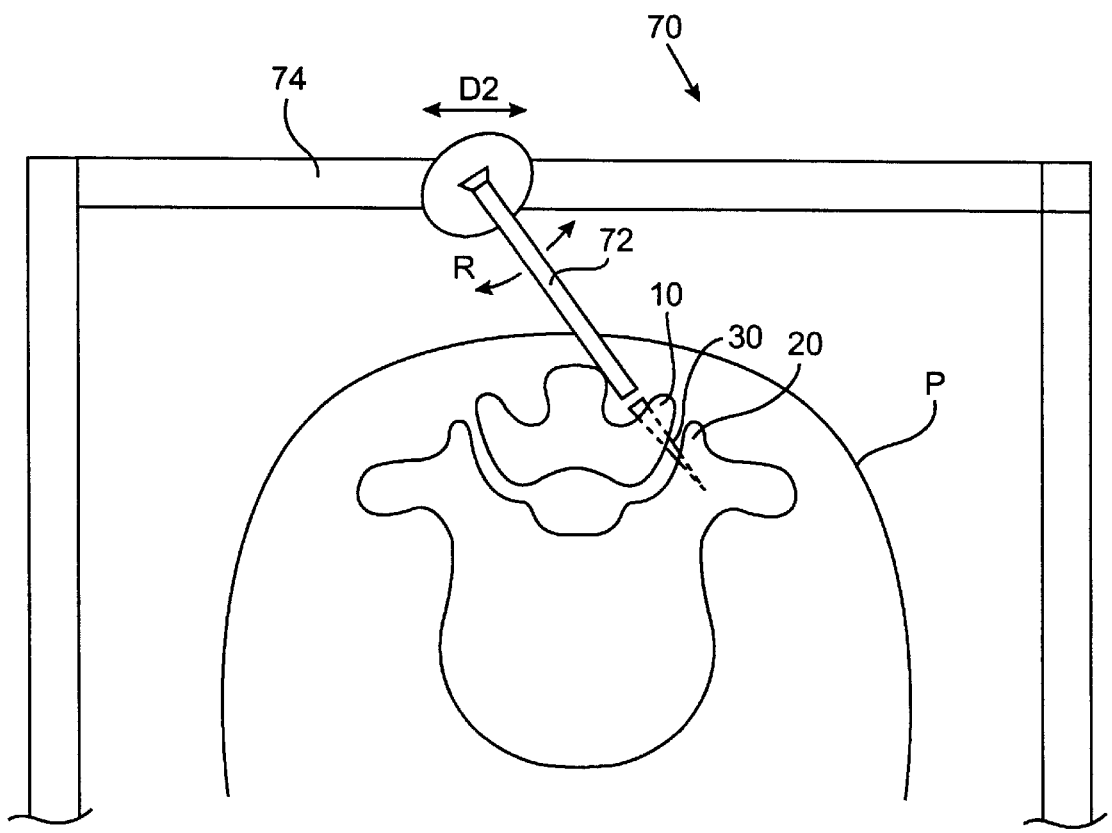
FIG. 4 is an illustration of placement of a pair of facet screws with the assistance of a rectangular coordinate surgical guideframe.

Placement of facet screws 30A and 30B may then be carried out after placement of bone allografts 40A and 40B. (The present invention, however, is not so limited, i.e.: the facet screws may be positioned prior to positioning the bone allografts). Most preferably, the placement of facet screws 30A and 30B is carried out using the same guideframe as was used to position the bone allografts. For illustration purposes, however, FIG. 4 shows the positioning of facet screws 30A and 30B accomplished with a rectangular coordinate surgical guideframe 70. An example of such a rectangular coordinate surgical guideframe is set forth in copending U.S. patent application Ser. No. 09/326,739, filed Jun. 4, 1999, and U.S. Provisional Patent Applications No. 60/120,663, filed Feb. 19, 1999 and No. 60/129,702, filed Apr. 16, 1999, all incorporated herein by reference in their entirety. Cannula 70 is preferably positionable back and forth along cross member 74, and is rotatable in direction R. In a preferred aspect, as illustrated, cannula 72 is angled to facilitate the positioning of one of facet screws 30 therethrough in a transfacet approach.

In optional aspects, the positioning of cannulae 60 and 62 (or 72) can be accomplished in accordance with the novel image intensifier (C-arm reticle) systems as set forth in copending U.S. patent applications Ser. No. 09/326,740, filed Jun. 4, 1999, and Ser. No. 09/696,923, filed Oct. 25, 2000, and U.S. Provisional Patent Application No. 60/120, 663, filed Feb. 19, 1999, all incorporated herein by reference in their entirety.

In optional preferred aspects, bone allografts 40 are fabricated from an outer portion of a donor patient's femur bone with curved front end 41 comprising an outer surface of the femur bone. When fabricated in this manner, curved front end 41 will comprise the hardest (cortical) portion of the allograft. Placing curved front end 41 at or near the curved outer perimeter (i.e.: near the side, front) of the vertebrae 50 and 52 will thus result in positioning the preferably hardest part of allograft 40 (i.e.: curved front end 41) on the hardest (cortical) portion (ie. the outer edges) of the vertebrae 50 and 52.

While the exemplary embodiments have been described in some detail, by way of example and for clarity of understanding, a variety changes, adaptations, and modifications will be obvious to those of skill in the art. Hence, the scope of the present invention is limited solely by the appended claims.

What is claimed is:

1. A method of providing support between two adjacent vertebrae, comprising:
    positioning a pair of allografts between the two adjacent vertebrae at a location towards the anterior portion of the adjacent vertebrae; and
    securing together facet joints between the two adjacent vertebrae with a pair of facet screws, wherein said facet screws are positioned in at least one of a transfacet and translaminar approach.

2. The method of claim 1, wherein each of the bone allografts are positioned adjacent to a curved outer perimeter of the two adjacent vertebrae.

3. The method of claim 1, wherein the bone allografts are positioned at an angle to one another.

4. The method of claim 3, wherein the angle is 30° to 160°.

5. The method of claim 3, wherein the angle is approximately 90° to 120°.

6. The method of claim 1, further comprising:
    positioning autologous bone graft material posterolaterally behind the bone allografts.

7. The method of claim 1, further comprising:
    positioning autologous bone graft material positioned between and to the rear of the bone allografts.

8. The method of claim 1, further comprising:
    harvesting autologous bone graft material from an iliac crest.

9. The method of claim 1, wherein each of the bone allografts are advanced into position between the two adjacent vertebrae through a percutaneous cannula.

10. The method of claim 9, wherein the percutaneous cannula is disposed in a posterolateral approach.

11. The method of claim 9, wherein the percutaneous cannula is positioned by a surgical guideframe.

12. The method of claim 1, wherein each of the bone allografts are rotated by about 90° after insertion into the patient's intervertebral space.

13. The method of claim 1, wherein a first bone allograft is advanced into position between the two adjacent vertebrae through a first percutaneous cannula and the second bone allograft is advanced into position between the two adjacent vertebrae through a second percutaneous cannula.

14. The method of claim 13, wherein the first and second percutaneous cannulae are disposed in opposite posterolateral approaches.

15. The method of claim 1, wherein the facet screws are advanced into contact with the facet joints through a percutaneous cannula.

16. The method of claim 15, wherein the percutaneous cannula is positioned by a surgical guideframe.

17. A method of providing support between two adjacent vertebrae, comprising:
    positioning a pair of bone allografts between the two adjacent vertebrae at a location towards the anterior portion of the adjacent vertebrae and at an angle to one another; and
    securing together facet joints between the two adjacent vertebrae with a pair of facet screws.

18. The method of claim 17, wherein the angle is 30° to 160°.

19. The method of claim 17, wherein the angle is approximately 90° to 120°.

20. A method of providing support between two adjacent vertebrae, comprising:
    positioning a pair of bone allografts between the two adjacent vertebrae at a location towards the anterior portion of the adjacent vertebrae;
    securing together facet joints between the two adjacent vertebrae with a pair of facet screws; and
    positioning autologous bone graft material posterolaterally behind the bone allografts.

21. A method of providing support between two adjacent vertebrae, comprising:
    positioning a pair of bone allografts between the two adjacent vertebrae at a location towards the anterior portion of the adjacent vertebrae;

securing together facet joints between the two adjacent vertebrae with a pair of facet screws; and positioning autologous bone graft material positioned between and to the rear of the bone allografts.

22. A method of providing support between two adjacent vertebrae, comprising:

positioning a pair of bone allografts between the two adjacent vertebrae at a location towards the anterior portion of the adjacent vertebrae;

securing together facet joints between the two adjacent vertebrae with a pair of facet screws; and harvesting autologous bone graft material from an iliac crest.

23. A method of providing support between two adjacent vertebrae, comprising:

positioning a pair of bone allografts between the two adjacent vertebrae at a location towards the anterior portion of the adjacent vertebrae, wherein a first bone allograft is advanced into position between the two adjacent vertebrae through a first percutaneous cannula and the second bone allograft is advanced into position between the two adjacent vertebrae through a second percutaneous cannula; and securing together facet joints between the two adjacent vertebrae with a pair of facet screws.

24. The method of claim 23, wherein the first and second percutaneous cannulae are disposed in opposite posterolateral approaches.

* * * * *